United States Patent

Neri et al.

Patent Number: 5,568,818
Date of Patent: Oct. 29, 1996

[54] METHOD AND DEVICE FOR DETERMINING THE DENSITY OF A STREAM OF FIBROUS MATERIAL ON A CIGARETTE MANUFACTURING MACHINE

[75] Inventors: Armando Neri, Bologna; Giancarlo Santin, San Lazzaro Di Savena; Giovanni Squarzoni, Argelato, all of Italy

[73] Assignee: G.D Societa' Per Azioni, Bologna, Italy

[21] Appl. No.: 349,080

[22] Filed: Dec. 2, 1994

[30] Foreign Application Priority Data

Dec. 3, 1993 [IT] Italy .................. BO93A0487

[51] Int. Cl.$^6$ ................ A24C 5/14; A24C 5/39
[52] U.S. Cl. .............. 131/84.4; 73/74; 131/905; 131/906
[58] Field of Search ................ 131/84.1, 84.4, 131/905, 906, 909, 910; 73/74

[56] References Cited

U.S. PATENT DOCUMENTS 1,878,109  9/1932  Clark .................. 131/910 X
2,535,027  12/1950  Anderson ............. 131/910 X
4,045,657  8/1977  Falke .................. 131/910 X
4,942,363  7/1990  Lowitz ................ 131/905 X

*Primary Examiner*—Jennifer Bahr
*Attorney, Agent, or Firm*—Ladas & Parry

[57] ABSTRACT

To determine the density of a stream of fibrous material on a cigarette manufacturing machine, two different measurements are performed, the first of which is capacitive and supplies a first signal as a function of the density of the dry component and of the density of the liquid in the stream of fibrous material, and the second of which is ultrasonic and supplies a second signal indicating the density of the dry component; the second signal is combined with the first signal to obtain a third signal indicating the density of the liquid in the stream of fibrous material; and, from the third and second signals, a fourth signal is obtained indicating the density of the stream of fibrous material as the sum of the density of the dry component and of the liquid in the stream of fibrous material.

11 Claims, 4 Drawing Sheets

METHOD AND DEVICE FOR DETERMINING THE DENSITY OF A STREAM OF FIBROUS MATERIAL ON A CIGARETTE MANUFACTURING MACHINE

BACKGROUND OF THE INVENTION

The present invention relates to a method and device for determining the density of a stream of fibrous material on a cigarette manufacturing machine.

In the following description, reference is made purely by way of example to a cigarette manufacturing machine and to determination of the tobacco density of a continuous cigarette rod.

As is known, on cigarette manufacturing machines, a suction conveyor belt draws the tobacco from a tank and deposits it on to a continuous strip of paper; the longitudinal edges of the paper strip are then folded one on top of the other about the tobacco; and the continuous cigarette rod so formed is fed to a cutting station where it is cut into single or double cigarettes.

The tobacco is normally supplied in such a manner as to be distributed unevenly inside the cigarette, and more specifically in such a manner as to be denser at the two ends than in the center, to prevent tobacco fallout and detachment of the filter from the cigarette, and at the same time ensure correct ventilation of the intermediate portion of the cigarette. This is achieved by supplying a greater quantity of tobacco at the ends of the cigarette as compared with the center, for which purpose, a rotary shaving device is provided along the path of the tobacco on the conveyor, for shaving it into the contour corresponding to the required density. The shaving device is both height adjustable for controlling the mean quantity of tobacco in each cigarette (mean density or weight), and time adjustable for obtaining a maximum quantity of tobacco at the point at which the continuous cigarette rod is cut (adjacent ends of two cigarettes); which adjustment is made according to the discrepancy between the desired distribution of the tobacco and the actual distribution determined on the cigarette rod upstream from the cutting station.

Various solutions currently exist for determining the actual distribution of the tobacco, most of which feature a beta-ray sensor comprising a radioactive source and a beta ray detector located on either side of the cigarette rod, along the path of the rod between the forming and cutting stations. The radioactive source typically comprises a strontium (Sr90) pellet, and is housed inside a shielded container with a hole facing the cigarette rod; and the detector comprises an ionization chamber and an electrometer for measuring the energy of the incoming radiation. On the basis of fluctuations in the incoming radiation, an electronic system connected to the detector determines the variation in the density of the tobacco and controls the shaving knife accordingly.

Though precise and reliable, the above solution creates numerous problems, mainly due to the use of harmful radiation which, on the one hand, requires special care and procedures on the part of the operators, and, on the other, poses problems for disposing of the depleted pellets. All these problems are further compounded by the energy of the emitted radiation being correlated to the traveling speed of the cigarette rod, and by the current tendency to produce increasingly fast-operating machines therefore requiring greater amounts of energy. As a result, alternative solutions have been devised featuring different types of sensors, the efficiency of which, however, is impaired by the sensors being sensitive to different parameters such as the humidity, colour and more or less fibrous structure of the tobacco.

SUMMARY OF THE INVENTION

It is an object of the present invention to provide an accurate, reliable method and device for determining the mass of tobacco in the stream of material, without using sensors involving harmful radiation.

According to the present invention, there is provided a method of determining the density of a stream of fibrous material on a cigarette manufacturing machine, said stream of fibrous material comprising a dry component and a liquid in varying unknown proportions; characterized in that it comprises the steps of:

effecting a first capacitive measurement for obtaining a first signal as a function of the density of the dry component and of the density of the liquid in said stream of fibrous material;

effecting a second ultrasonic measurement for obtaining a second signal correlated to the density of the dry component in said stream of fibrous material; and generating, on the basis of said first and second signals, a third signal indicating the density of said stream of fibrous material.

According to the present invention, there is also provided a device for determining the density of a stream of fibrous material on a cigarette manufacturing machine, said stream of fibrous material comprising a dry component and a liquid in varying unknown proportions; characterized in that it comprises:

a first capacitive sensor for generating a first signal as a function of the density of the dry component and of the density of the liquid in said stream of fibrous material;

a second ultrasonic sensor for generating a second signal correlated to the density of the dry component in said stream of fibrous material; and first generating means supplied with said first and second signals and generating a third signal indicating the density of said stream of fibrous material.

BRIEF DESCRIPTION OF TEE DRAWINGS

A number of non-limiting embodiments of the present invention will be described by way of example with reference to the accompanying drawings, in which.

DETAILED DESCRIPTION OF TEE INVENTION

Figure 1:
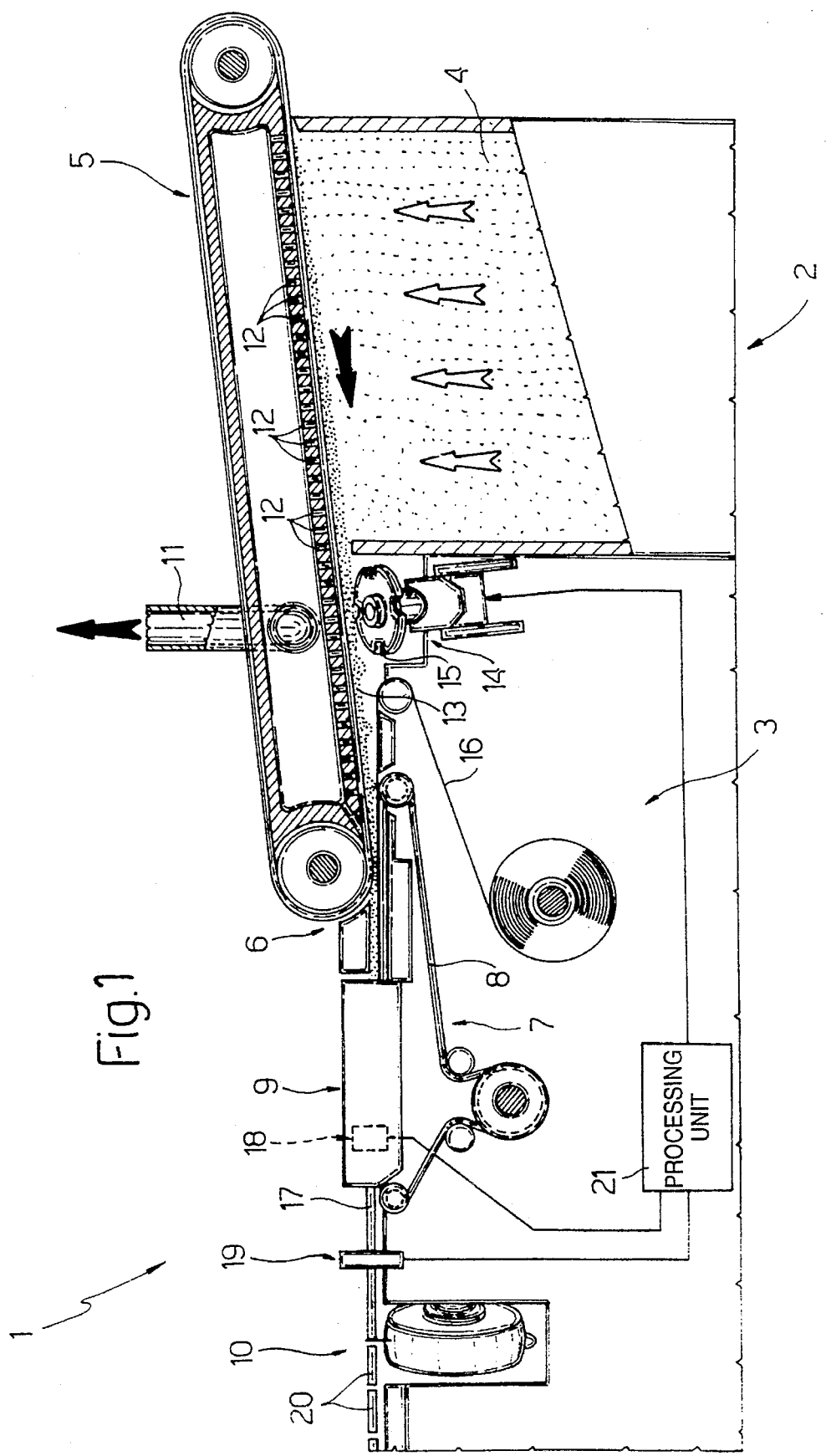
FIG. 1 shows a schematic view of a cigarette manufacturing machine featuring a first embodiment of the device according to the present invention.

Number 1 in FIG. 1 indicates a cigarette manufacturing machine comprising a tobacco feed unit 2 (shown only partially) and a paper feed unit 3. Of tobacco feed unit 2 are shown only an upflow duct 4, and a conveyor 5 extending between duct 4 and a tobacco unloading station 6; and paper feed unit 3 comprises a conveyor 7 with a belt 8, a forming beam 9, and a cutting station 10. In known manner, conveyor 5—which presents a vacuum inside generated by conduit 11, and holes 12 along its bottom branch—draws the tobacco from duct 4 to form a continuous layer 13; and along the path of the tobacco, beneath conveyor 5, a rotary shaving device 14 with recesses 15 removes the surplus tobacco in known, differential manner to achieve a predetermined contour of continuous layer 13.

At unloading station 6, the shaved tobacco layer is deposited on to a continuous strip of paper 16, the two longitudinal edges of which are folded one on top of the other and gummed on forming beam 9 to form a continuous cigarette rod 17. Along the path of rod 17, there are provided two sensors 18, 19 forming part of the device according to the invention for determining the distribution of the tobacco inside rod 17, and of which sensor 18 is located inside beam 9 downstream from the formation of rod 17, and sensor 19 is located at the output of beam 9 upstream from cutting station 10. Rod 17 is then fed through cutting station 10 where it is cut into cigarette portions 20. Though not shown in FIG. 1, the components of machine 1, with the exception of duct 4, are duplicated to form two side by side, parallel-operating lines.

Sensors 18 and 19 are connected to a processing unit 21 for processing the signals generated by sensors 18, 19 and determining the actual distribution of the tobacco in rod 17, and which, depending on the extent to which this differs from the predetermined distribution, adjusts the height and timing of shaving device/s 14. Processing unit 21 also provides for other functions such as calculating statistics, discrepancy percentages, etc.

Figure 2:
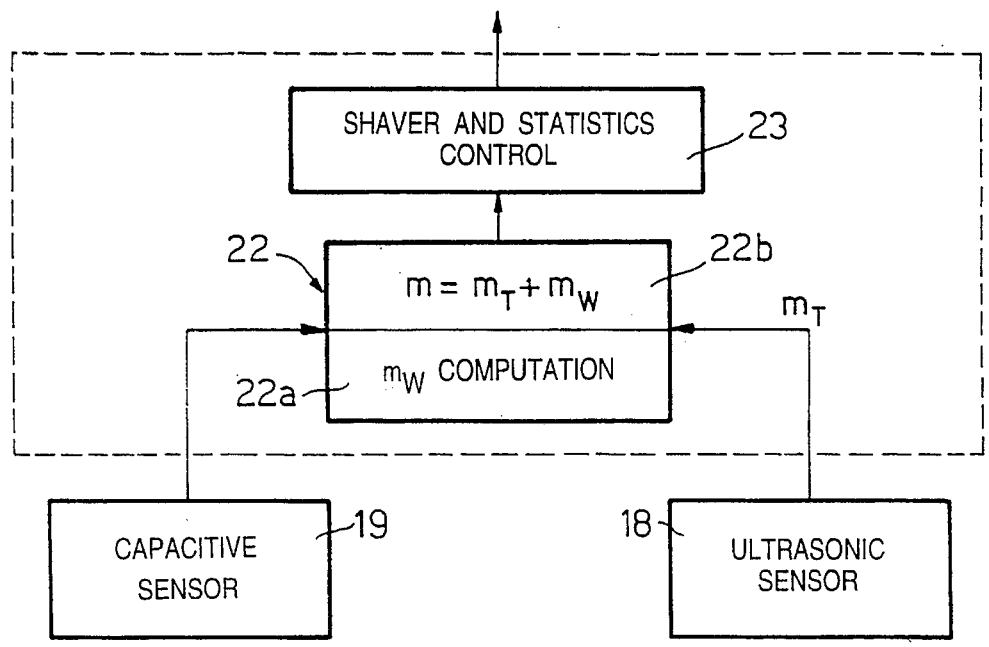
FIG. 2 shows a block diagram of the device according to the present invention.

The signals supplied by sensors 18, 19 are combined for accurately determining the actual distribution of the tobacco inside rod 17, as shown in FIG. 2. In more detail, sensor 19 is a capacitive sensor, the capacitance of which depends on both the dry tobacco and water content of the cigarette rod, and the appropriately processed output signal of which therefore varies according to the equation:

$$DC = K1 \, mT \, (K2 + mW/mT)$$

wherein K1 and K2 are two constants depending in known manner on the sensor, tobacco and water characteristics; and mT is the mass of dry tobacco and mW the mass of water in the cigarette rod.

Figure 3:
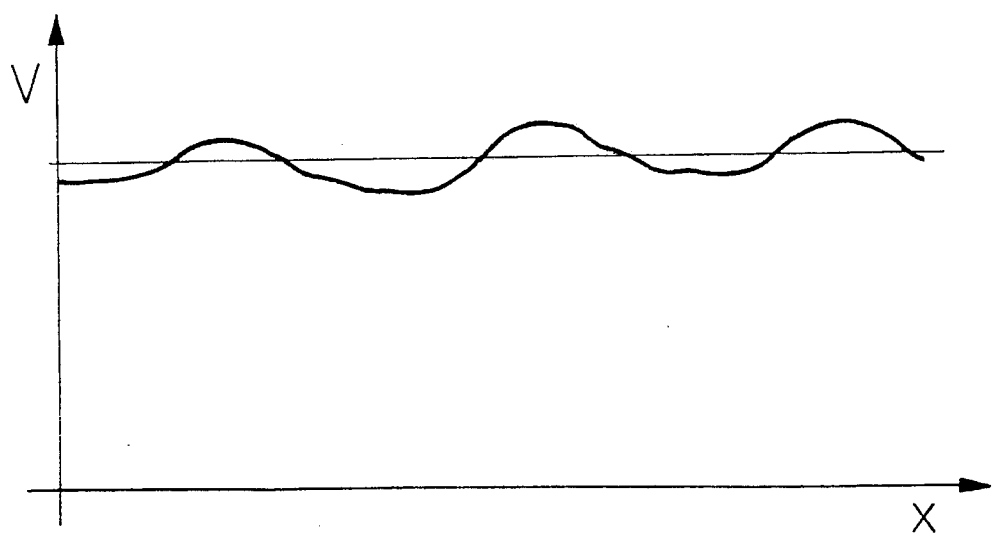
FIG. 3 shows a laboratory test diagram of the tobacco contour determined by the capacitive sensor.

Capacitive sensor 19 therefore supplies a voltage output signal (FIG. 3) accurately reproducing the mass (density) of the tobacco along the cigarette rod, but which is highly sensitive to the water content of the rod. Due to the differing dielectric properties involved, the capacitive sensor in fact is far more sensitive to water than to the dry tobacco. Moreover, as the output signal of the capacitive sensor is not directly related to the total density of the rod, i.e. to the total density of the two components, the capacitive sensor alone is incapable of measuring the density of the rod or even distinguishing between the contribution made by the dry tobacco and the water.

To calculate the actual mass of material (dry tobacco and water) in the rod, the mass (density) of the dry tobacco is measured separately to distinguish the dry tobacco contribution from that of the water in the output signal of capacitive sensor 19 and so calculate the total density (mass). As ultrasonic sensors with appropriately selected frequencies are insensitive to humidity in the material under examination, so that the output signal directly indicates the mass mT of dry tobacco, the second measurement is made using second ultrasonic sensor 18.

As ultrasonic sensor 18 on its own is also incapable of supplying the total density of rod 17, by entering into (1) the mT value measured by sensor 18, it is possible to determine the mass of water mW and, by adding this to the mass of dry tobacco, the total mass. The mass of dry tobacco and water may be calculated with reference to very small portions of the rod (practically the volume "viewed" by the sensors) for achieving a substantially point-by-point density pattern, or with reference to rod portions of predetermined length for obtaining the mean dry tobacco and water mass value over said portions. In the latter case, it is possible to obtain the mean total density value, while the variation in the total density of the rod is given by the capacitive signal.

The output signals of sensors 18 and 19 are supplied to a unit 22 for determining the density of the water and the total density of the material in rod 17. As already stated, unit 22 is divisible theoretically into two sections: a section 22a for calculating the mass (density) of the water in the rod material; and a section 22b for calculating the total mass (density) of the rod material by adding the mass (density) of the dry tobacco and water in the rod. The output signal of unit 22 is then supplied to a unit 23 which, on the basis of the required distribution of material in rod 17, generates control signals in known manner for adjusting the height and timing of shaving device 14 (FIG. 1).

Unit 23 also provides for statistical processing, and for determining other information on the basis of the sensor signals, such as humidity on the basis of the ratio between the water and dry tobacco mass (mW/mT). Units 22, 23 conveniently all form part of processing unit 21.

Figure 4:
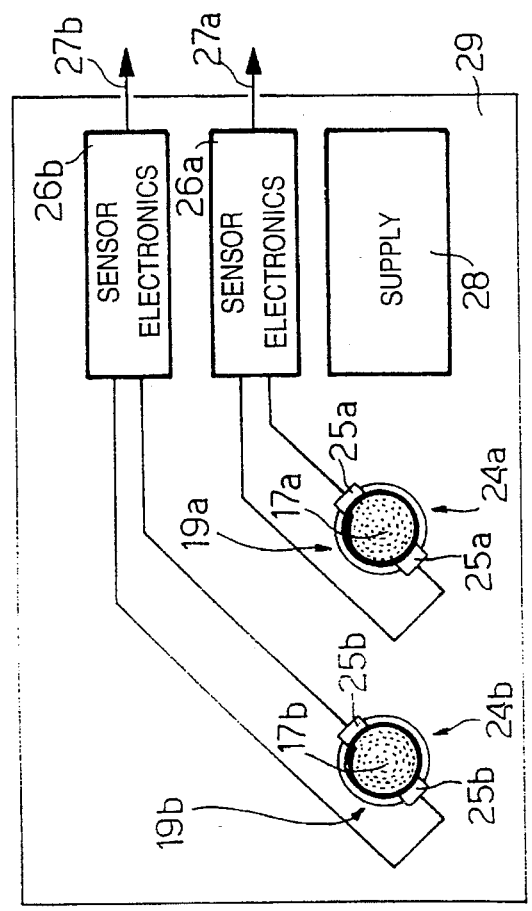
FIG. 4 shows a machine cross section illustrating a detail of the device according to the invention.

A possible location of capacitive sensor 19 is shown in FIG. 4 which shows the two lines 24a, 24b of the machine, the cross sections of the two rods, here indicated 17a, 17b, and the respective sensors 19a, 19b.

Each capacitive sensor 19a, 19b comprises a respective pair of electrodes 25a, 25b, and a respective electronic signal processing and control circuit 26a, 26b. The respective output signals of electronic circuits 26a, 26b are supplied to processing unit 21 (FIG. 1) over respective lines 27a, 27b; and provision is also made for a single supply unit 28 and a housing 29.

Figure 5:
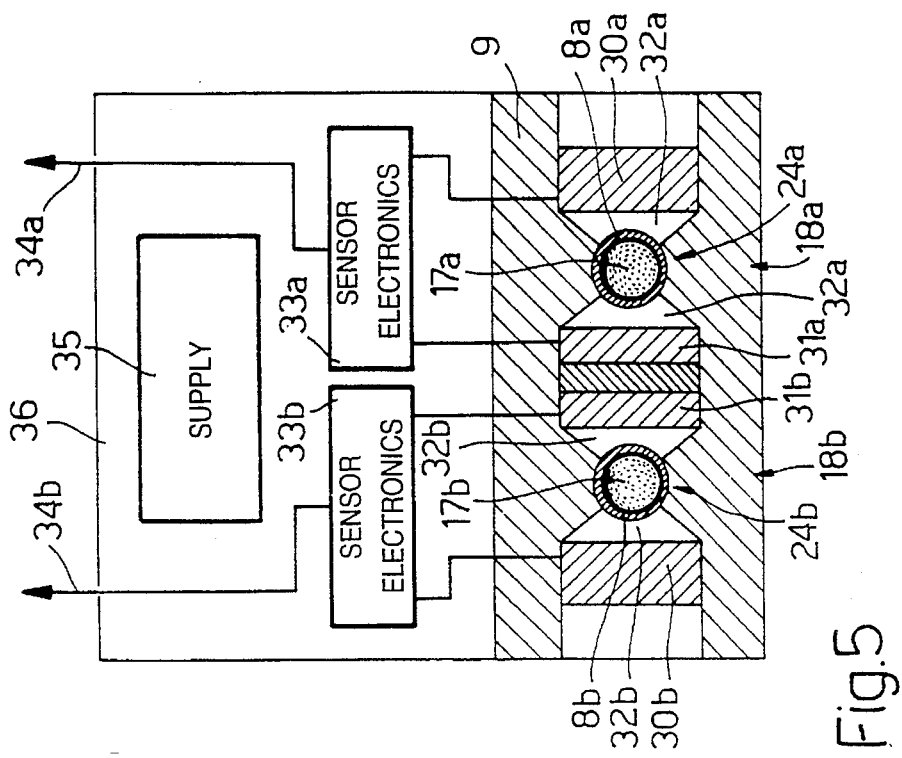
FIG. 5 shows a machine cross section illustrating a further detail of the device according to the invention.

To maximize its sensitivity, ultrasonic sensor 18 is mounted inside and close to the output of forming beam 9 (FIG. 1), in such a position that rod 17 is already formed (paper strip edges already gummed) but is still surrounded by belt 8 of paper conveyor 7, as shown in FIG. 5 which illustrates one possible embodiment of the ultrasonic sensor.

FIG. 5 shows two ultrasonic sensors 18a, 18b, one each for lines 24a, 24b and each comprising a respective ultrasonic transmitter 30a, 30b; a respective ultrasonic receiver (microphone) 31a, 31b; and a respective pair of adapter cones 32a, 32b formed in the body of beam 9. Ultrasonic transmitters 30a, 30b and receivers 31a, 31b are connected to respective electronic signal processing and control circuits 33a, 33b as explained in more detail with reference to FIG. 8; and the outputs of electronic circuits 33a, 33b are connected to processing unit 21 over respective lines 34a, 34b. Provision is also made for a single supply unit 35 and a housing 36.

Figure 6:
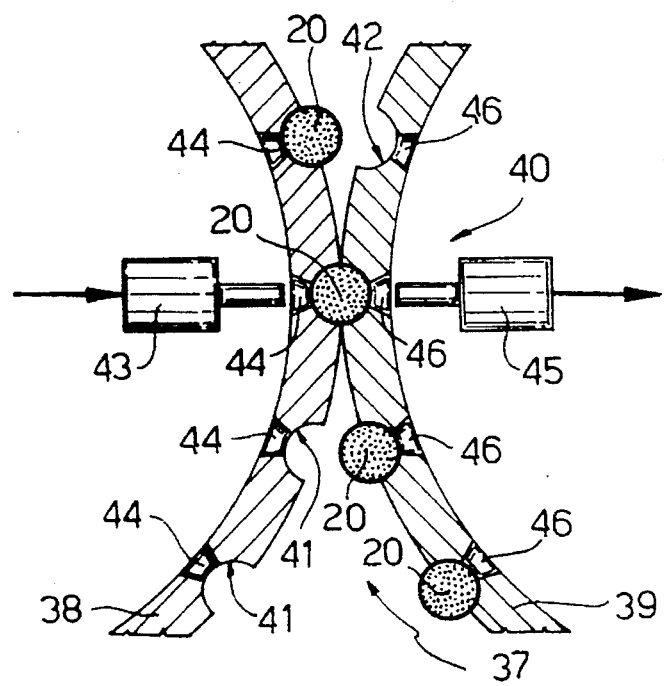
FIG. 6 shows a cross section of a cigarette manufacturing machine, illustrating a variation of a detail of the device according to the invention.

According to a variation of the invention, the ultrasonic sensor may be located downstream from machine 1, in the filter assembly machine, as shown schematically in FIG. 6.

With reference to FIG. 6, the filter assembly machine 37 comprises a pair of hollow drums or rollers 38, 39 (shown partially) for transferring cigarette portions 20 from seats 41 on drum 38 to seats 42 on drum 39. In the example shown, the ultrasonic sensor 40 is mounted partly on drum 38 and partly on drum 39, and the two parts cooperate to determine the density of the dry tobacco during transfer of cigarette portion 20 when the two parts face each other. In the example shown, the transmitter 43 is mounted (in a manner not shown) inside drum 38, integral with the casing of machine 1; the receiver 45 is mounted inside drum 39, also integral with the casing of machine 1; and drums 38, 39 present respective holes 44, 46 at respective seats 41, 42 for the passage of the pressure waves generated by transmitter 43. When a cigarette portion 20 is transferred from first drum 38 to second drum 39, holes 44 and 46 of respective seats 41, 42 are located along the same axis of sensor 40 (the axis connecting transmitter 43 to receiver 45) thus permitting ultrasonic exploration of cigarette portion 20.

By appropriately shaping the holes or installing a number of source-detector pairs, the above embodiment provides for examining either a portion or the whole length of cigarette portion 20. Changes may also be made to the mechanical arrangement in FIG. 6, to provide airtight graphite surfaces between the moving parts (sliding surfaces).

Figure 7:
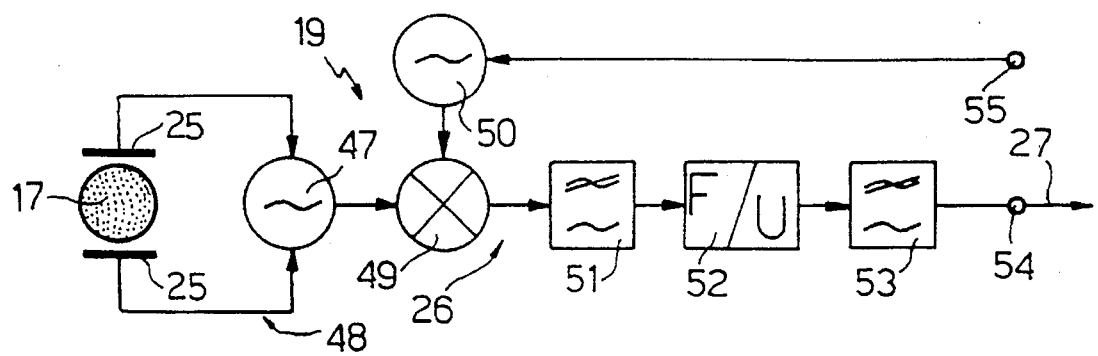
FIGS. 7 and 8 show circuit diagrams of the sensors featured in the device according to the invention.

FIG. 7 shows an electric diagram of capacitive sensor 19, including electronic signal processing and control circuit 26. In FIG. 7, the two electrodes 25 on either side of continuous cigarette rod 17 constitute, together with a circuit 47, a high-frequency oscillating circuit 48, the frequency of the oscillating output signal of which varies alongside a variation in the capacitance of the electrode 25/rod 17 group, and is proportional to the mass of tobacco and the mass of water in the material traveling between the two electrodes.

In a multiplier 49, the output signal of oscillating circuit 48 is multiplied by a reference signal generated by an oscillator 50, to give an oscillating signal with a frequency equal to the difference between the frequencies of the output signal of oscillating circuit 48 and the reference signal. The output signal of multiplier 49 is filtered in a low-pass filter 51 and converted into a voltage signal by a frequency/voltage converter 52, the output signal of which is then filtered in a low-pass filter 53 and supplied to output 54 connected over line 27 to processing unit 21 (FIG. 1). An input 55 is connected to reference oscillator 50, for adjusting and calibrating the reference oscillating signal.

Figure 8:
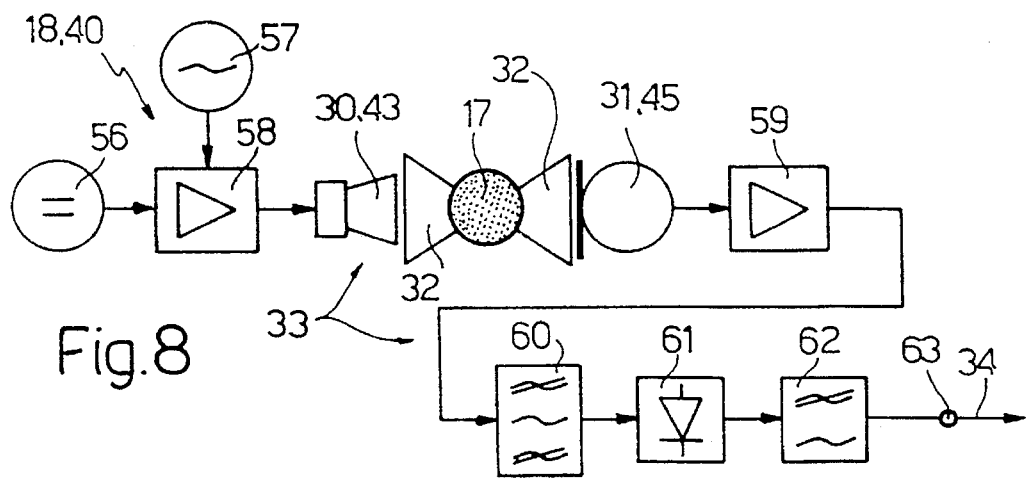

FIG. 8 shows an electric diagram of ultrasonic sensor 18, 40, including electronic signal processing and control circuit 33. Circuit 33 comprises a bias generator 56, and a modulating or noise generator 57, the outputs of which are connected to a drive element 58 controlling ultrasonic transmitter 30, 43. The wide-band ultrasonic receiver or microphone 31, 45 is connected to an amplifier 59 cascade-connected to a band-pass filter 60, a rectifier 61, and a low-pass filter 62 whose output 63 defines the output of electronic circuit 33 and is connected over line 34 to processing unit 21.

In actual use, sensors 18, 19 generate two separate signals correlated to the characteristics of the continuous cigarette rod, and which are sampled with reference to successive sections of the rod and processed as described for accurately and reliably determining the total mass (density) of the tobacco instant by instant; which density measurement is used for correcting the distance between the shaving device and conveyor belt 5 and so varying the mean mass (density) of the tobacco, and for briefly slowing down or accelerating rotation of the shaving device (timing adjustment) to adjust the thickest tobacco point (the ends of the finished cigarettes).

The cooperation of two sensors—one capacitive and the other ultrasonic—is therefore essential for accurate control of the shaving device independent of external influences (humidity, colour and structure of the tobacco).

By eliminating the use of harmful radiation sources, the device according to the present invention therefore provides for greatly simplifying handling, maintenance and part replacement procedures.

What is claimed is:

1. A method of determining the density of a stream of fibrous material (17) on a cigarette manufacturing machine (1), said stream of fibrous material (17) comprising a dry component and a liquid in varying unknown proportions; said method comprising the steps of:

effecting a first capacitive measurement for obtaining a first signal indicating a quantity which may be expressed as a function of the density of the dry component and of the density of the liquid in said stream of fibrous material;

effecting a second ultrasonic measurement for obtaining a second signal correlated to the density of the dry component in said stream of fibrous material; and generating, on the basis of said first and second signals, a third signal indicating the density of said stream of fibrous material.

2. A method as claimed in claim 1, characterized in that said step of generating a third signal comprises the steps of generating, on the basis of said first and second signals, a fourth signal indicating the density of the liquid in said stream of fibrous material; and adding said second signal to said fourth signal.

3. A method as claimed in claim 1, characterized in that it comprises the step of calculating the mean value of said second signal over a portion of said stream of fibrous material; and said step of generating a third signal comprises the step of determining the mean density of said stream of fibrous material on the basis of said first signal and said mean value of said second signal.

4. A device for determining the density of a stream of fibrous material (17) on a cigarette manufacturing machine (1), said stream of fibrous material (17) comprising a dry component and a liquid in varying unknown proportions; said method comprising:

a first capacitive sensor (19) for generating a first signal indicating a quantity which may be expressed as a function of the density of the dry component and of the density of the liquid in said stream of fibrous material;

a second ultrasonic sensor (18, 40) for generating a second signal correlated to the density of the dry component in said stream of fibrous material; and first generating means (22) supplied with said first and second signals and generating a third signal indicating the density of said stream of fibrous material.

5. A device as claimed in claim 4, characterized in that said first generating means (22) comprises second generating means (22a) supplied with said first and second signals and generating a fourth signal indicating the density of the liquid in said stream of fibrous material; and adding means (22b) for adding said second signal to said fourth signal.

6. A device as claimed in claim 4 characterized in that said first generating means (22) forms part of a central processing unit (21).

7. A device as claimed in claim 4, for a manufacturing machine (1) having a stream forming unit (9) and a cigarette cutting section (10); characterized in that at least said first sensor (19) is located between said stream forming unit (9) and said cigarette cutting section (10) of said machine.

8. A device as claimed in claim 7, characterized in that said second ultrasonic sensor (18) is located inside said stream forming unit (9).

9. A device as claimed in claim 7, wherein, downstream from said manufacturing machine (1), there is provided a filter assembly machine (37) having a first and second drum (38, 39); characterized in that said second ultrasonic sensor (40) comprises a part (43) associated with said first drum (38), and a part (45) associated with said second drum (39).

10. A device as claimed in claim 4, characterized in that said capacitive sensor (19) comprises an oscillating circuit (48) in turn comprising a pair of electrodes (25) along the path of said stream of fibrous material (17); a reference-frequency voltage generator (50); a multiplier (49) connected to said oscillating circuit (48) and to said reference-frequency voltage generator (50); and a frequency/voltage converter (52) connected to said multiplier (49) and generating a voltage signal correlated to the density of the dry component and the liquid in said stream of fibrous material (17).

11. A device as claimed in claim 4, characterized in that said ultrasonic sensor (18; 40) comprises an ultrasonic emitter (30; 43); a first hollow conical adapter element (32; 44) adjacent to said ultrasonic emitter, and a second hollow conical adapter element (32; 46), said adapter elements being adjacent to the path of said stream of fibrous material (17); an ultrasonic microphone (31; 45) adjacent to said second adapter element (32; 46); and amplifying (59), filtering (60, 62) and rectifying (61) means connected to said ultrasonic microphone (31; 45).

* * * * *